United States Patent
Rijken et al.

(10) Patent No.: US 8,769,922 B2
(45) Date of Patent: Jul. 8, 2014

(54) GUIDANCE CHAIN FOR GUIDING CABLES OR OTHER LINES IN A MEDICAL DIAGNOSTIC APPARATUS

(75) Inventors: Antonius Maria Rijken, Nuenen (NL); Martinus Antonius Maria Cuppen, Mierlo (NL); Ravindra Bhat, Eindhoven (NL); Arthur Robert Van Es, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 265 days.

(21) Appl. No.: 13/375,636

(22) PCT Filed: Jun. 21, 2010

(86) PCT No.: PCT/IB2010/052791
§ 371 (c)(1),
(2), (4) Date: Dec. 1, 2011

(87) PCT Pub. No.: WO2010/150172
PCT Pub. Date: Dec. 29, 2010

(65) Prior Publication Data
US 2012/0085078 A1    Apr. 12, 2012

(30) Foreign Application Priority Data

Jun. 26, 2009 (EP) .................... 09163912

(51) Int. Cl.
*F16G 13/16* (2006.01)
*F16G 13/02* (2006.01)

(52) U.S. Cl.
USPC .................. 59/78.1; 59/900; 248/49; 248/51

(58) Field of Classification Search
USPC .............. 72/78.1, 93, 900; 248/49, 68.1; 474/206, 207
See application file for complete search history.

(56) References Cited

U.S. PATENT DOCUMENTS

| 4,807,432 | A * | 2/1989 | Mauri .............................. 248/49 |
| 6,387,002 | B1 * | 5/2002 | Gunter ............................ 59/900 |
| 2002/0029555 | A1 * | 3/2002 | Komiya et al. ................ 59/78.1 |
| 2002/0108365 | A1 * | 8/2002 | Blase et al. .................... 59/78.1 |
| 2002/0124548 | A1 * | 9/2002 | Blase .............................. 59/78.1 |
| 2003/0136456 | A1 * | 7/2003 | Blase .............................. 59/78.1 |
| 2003/0182924 | A1 * | 10/2003 | Tsutsumi et al. .............. 59/78.1 |

FOREIGN PATENT DOCUMENTS

| DE | 4319598 A1 | 12/1994 |
| EP | 0277389 A1 | 8/1988 |
| WO | 2007132419 A2 | 11/2007 |
| WO | 2009132419 A1 | 11/2009 |

* cited by examiner

*Primary Examiner* — David B Jones (57) ABSTRACT

A guidance chain for guiding a connection line, such as a cable, electrical cable, fiber glass cable, water line, gas line or fluid line, between parts of a medical diagnostic apparatus which are moved relative to each other, includes plural chain elements, where consecutive chain elements are moveable relative to each other about a respective imaginary or real rotation axis for realizing a folding movement of the guidance chain. The guidance chain is constructed such that it has a pre-set curvature in an unfolded state, and the radial extensions of the rotation axes are originating from substantially the same point in a folded state of the guidance chain.

13 Claims, 8 Drawing Sheets

GUIDANCE CHAIN FOR GUIDING CABLES OR OTHER LINES IN A MEDICAL DIAGNOSTIC APPARATUS

FIELD OF THE INVENTION

The invention relates to a guidance chain for guiding a connection line, such as an electrical cable, of a medical diagnostic apparatus, and a medical diagnostic apparatus comprising a frame, a curved member rotatable relative to the frame, and a guidance chain for guiding at least one connection line passing from the frame to the curved member.

BACKGROUND OF THE INVENTION

A medical diagnostic apparatus of the kind mentioned in the opening paragraph is known from WO 2007/132419 A2. This medical diagnostic apparatus comprises a frame that is supporting a C-arm such that the C-arm can be rotated relative to the frame. The C-arm is holding an X-ray source and opposite thereto an X-ray detector with a patient table arranged there between. At least one connection line extends between the frame and the C-arm. The medical diagnostic apparatus further comprises a hose for guiding this connection, wherein the hose is provided with a chain of reinforcement elements, the chain extending in the longitudinal direction of the hose. In this medical diagnostic apparatus, the reinforcement elements can be rotated with respect to each other about an axis that is perpendicular to the longitudinal axis of the hose while they are substantially rigidly connected in a direction along their rotation axis. The chain provides the benefit of a certain degree of rigidity to the hose while maintaining an optimum freedom of movement of the support with respect to the frame of the medical diagnostic apparatus.

However, in newer medical diagnostic apparatuses, the C-arm travels wider angles compared to the existing systems. Therefore, the connection line extending between the frame and the C-arm must be made longer. Such a longer connection line is likely to touch the floor that is to be avoided, or in general, takes up a lot of space for providing the respective chain for guiding the connection line.

SUMMARY OF THE INVENTION

It is an object of the invention to provide a guidance chain in order to improve the connection guidance between the frame and the member rotatable relative to the frame in a medical diagnostic apparatus.

This object is solved with a guidance chain and an apparatus according to the independent claims. Advantageous further developments are subject of the dependent claims.

According to an embodiment of the invention, there is provided a guidance chain for guiding at least one connection line (such as a cable, electrical cable, fiber glass cable, water line, gas line or fluid line) between parts of a medical diagnostic apparatus, which are moveable relative to each other, the guidance chain comprising plural (connected or non-connected) chain elements, wherein consecutive chain elements are moveable relative to each other about a respective imaginary or real rotation axis for realizing a folding movement of the guidance chain during which the guidance chain forms a loop, wherein the guidance chain is constructed such that it has a pre-set curvature in an unfolded state, and the radial extensions of the rotation axes are originating from substantially the same point in a folded state of the guidance chain. "Pre-set" means that the curvature is predetermined or pre-defined apart from the bending due to gravity, which is caused by material flexibility. This embodiment provides the advantage that the connection line can be guided between parts which are moved relative to each other such that the connection line can follow the movement without locking or an increase in friction. Moreover, since the guidance chain according to this embodiment conforms also to the curved shape of a curved part, it takes up less space and can more easily integrated into an apparatus having curved parts.

According to an embodiment of the invention, the curvature of the guidance chain is realized by providing the individual chain elements on their radially inner sides with a smaller longitudinal length than on their radially outer sides.

According to another embodiment of the invention, the chain elements are provided with hinges for connecting consecutive chain elements. This has the advantage of a better stability of the guidance chain. Further, the guidance chain is easier to install, since the guidance chain without the connection line acts as a single part.

Further, the guidance chain can be constructed such that the chain elements are provided with rolling elements. This feature reduces friction of the guidance chain with respect to the part which it is in contact with and reduces abrasion and noise during the folding movement of the guidance chain. Advantageously, these rolling elements are wheels, the rolling direction of which corresponds to the longitudinal direction of the guidance chain.

According to a yet further embodiment, the chain elements are provided at their longitudinal ends with protrusions or recesses corresponding the respective recesses or protrusions of a consecutive chain element such that the chain elements are aligned relative to each other. This increases the stability of the guidance chain in a direction of the rotation axes of the individual chain elements.

In another embodiment, the chain elements are held together by the at least one connection line which the chain elements are attached to. This way the connection line is multifunctional serving not only as an (electrical) connection, but also as a structural member of the guidance chain.

According to a further embodiment of the invention, the chain elements are provided on at least one longitudinal side with at least one bracket for holding the at least one connection line to be guided. This way, the connection line is easy to attach to the guidance chain which improves maintainability.

According to an embodiment of the invention, there is provided a medical diagnostic apparatus comprising a frame, a curved or arc-shaped member rotatable relative to the frame, and an above described guidance chain for guiding at least one connection line passing between the frame and the curved member, the guidance chain being in contact with the curved member along a contacting surface, wherein the pre-set curvature of the guidance chain is adapted to (or substantially corresponds to) the curvature of the curved member at the contacting surface. This embodiment provides the advantage that the connection line is guided between the frame and the curved member such that the connection line can follow the movement of the curved member relative to the frame without locking or an increase in friction. Moreover, since the guidance chain according to this embodiment conforms to the curved shape of the curved member, it is avoided that the guidance chain sooner or later hits the floor or the ceiling as it might be in case of the vertically positioned guidance chains of the state of the art. Therefore, a good lifetime can be expected and larger movements can be made. By guiding the connection lines by means of the guidance chain, bending of the connection lines with a not permitted radius can be avoided. The arrangement according to this embodiment enables the integration of the guidance chain inside the arc-shaped member.

According to a further embodiment of the invention, the guidance chain is integrated into the curved member. This embodiment provides the advantage of an improved cleanliness, cleanability and aesthetics of the whole system. Thus, the whole system is better cleanable. Further, this way, the whole system can be build in a more compact way. Moreover, the C-arm of a medical diagnostic apparatus can be shipped with the already integrated guidance chain.

According to another embodiment, the curvature of the guidance chain is realized by providing the individual chain elements on their sides facing the contacting surface with a curvature which substantially corresponds to the curvature of the curved member.

According to a further development of the invention, the curved member forms a duct which supports the guidance chain in directions perpendicular to the longitudinal direction of the curved member.

According to a further development, a hose is provided between the chain elements and the at least one connection line to be guided for protecting the connection line. This way the connection line is additionally protected against damage and abrasion, and in case of plural connection lines, this increases the tidiness of arrangement.

According to another embodiment, the curved member forms a duct which accomodates two guidance chains which are arranged such that they overlap with respect to the longitudinal direction of the curved member and the non-overlapping end portions of which point in opposite directions along the longitudinal direction of the curved member. This provides the advantage that the hollow inside of the curved member can be utilized more efficiently. Moreover, this provides the option to connect the curved member with two different parts which are moveable relative to the curved member.

In another embodiment, the curved element is a C-arm of an X-ray tube.

These and other aspects of the invention will be apparent from and elucidated with reference to the embodiments described hereafter.

It may be seen as the gist of the invention to provide a guidance chain for a connection line passing from a frame to a member moveable relative thereto, wherein the guidance chain has an inherent pre-set curvature within a plane substantially perpendicular to the folding movement of the guidance chain, wherein the curvature is adapted or substantially corresponds to the curvature of the moveable member such that the guidance chain can be integrated inside the moveable member.

DETAILED DESCRIPTION OF EMBODIMENTS

Figure 1:
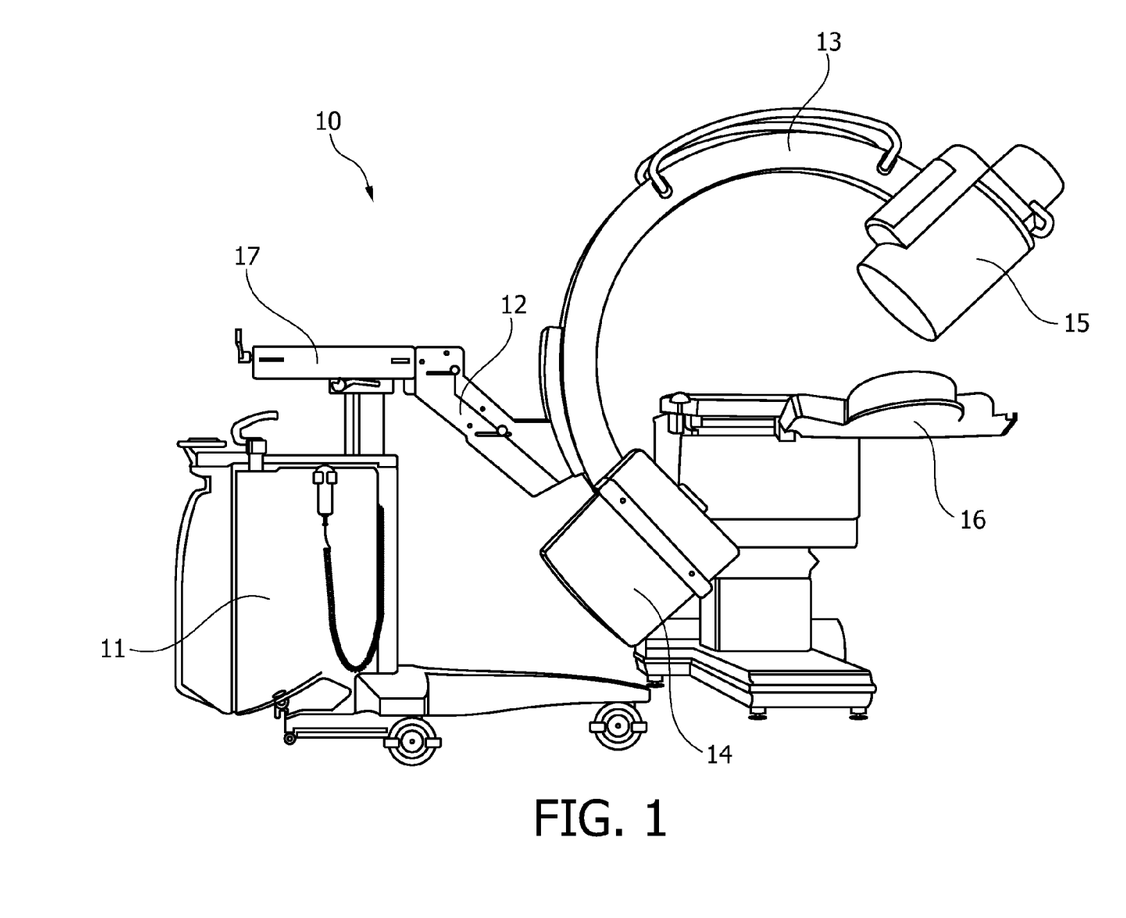
FIG. 1 shows an embodiment of a medical diagnostic apparatus according to the invention in a side view.

FIG. 1 shows an embodiment of a medical diagnostic apparatus 10 according to the invention in a side view. In this embodiment, the medical diagnostic apparatus is an X-ray apparatus 10. This X-ray apparatus 10 comprises a stand 11 that is placed on the floor and moveable by means of wheels attached thereto. The stand 11 holds a frame 12 of the X-ray apparatus 10 such that the frame 12 is movable in a vertical direction relative to the stand 11. Further, the X-ray apparatus 10 comprises a rotatable curved, arc-shaped or C-shaped member that is in this embodiment a so-called C-arm 13. In the depicted side view, the C-arm 13 has a semi-circular shape, wherein one end of the C-arm 13 is provided with an X-ray source 14 with a collimator and the other end is provided with an X-ray detector 15. The X-ray source 14 and the X-ray detector 15 are positioned diametrically opposite to each other in such a manner that they face each other. Between the X-ray source 14 and the X-ray detector 15, a patient table 16 is positioned, on which a patient to be diagnosed can lay.

The frame 12 moveably supports the C-arm 13 such that the C-arm 13 can be rotated about a rotation axis that is perpendicular to an imaginary plane including the semi-circular shape of the C-arm 13 and intersecting with the center of the semi-circular shape. In the following, this rotation axis is called rotation axis of the C-arm. Further, the C-arm 13 can be rotated about or slided along a horizontal shaft 17 integrated into the frame 12. Actually, the horizontal shaft 17 slides over a bearing block on top of a vertical column that itself is slidable up and down in the stand 11.

The X-ray source 14 and the X-ray detector 15 can be brought in position with respect to the patient table 16 or the patient laying on the table 16 by moving the frame 12 vertically relative to the stand 11, by rotating the C-arm 13 about the horizontal shaft 17 and/or by sliding the C-arm 13 along the horizontal shaft 17 and/or by rotating the C-arm 13 relative to the frame 12 about the rotation axis of the C-arm.

A plurality of connection lines which cannot be seen in FIG. 1 since they are integrated within the C-arm 13, extent between the C-arm 13 and the frame 12. The connection lines can be electrical supply cables for the X-ray source 14 and the X-ray detector 15, for the motors (not shown) for positioning the C-arm 13, for driving blades (not shown) of the collimator, for the viewfinder (not shown), for the collision protection mechanism (not shown) that is to prevent the X-ray detector 15 from hitting the patient, and so on. Further, there could be connection lines for high-voltage cables for supplying the high voltage between the cathode and the anode of the X-ray source 14. In this embodiment, the connection lines are preferably electrical cables, however, it is also within the scope of the invention that the connection lines could be fiber glass cables, flexible water lines, flexible gas lines or flexible fluid lines, for example for cooling the X-ray source 14 and/or the X-ray detector 15.

Figure 2:
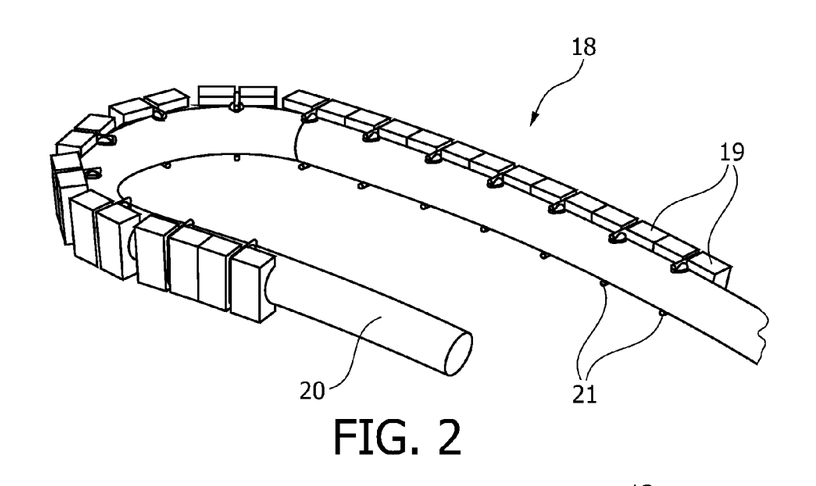
FIG. 2 shows a guidance chain for guiding the at least one connection line between a frame and a C-arm of the medical diagnostic apparatus.

FIG. 2 shows a guidance chain 18 for guiding the at least one connection line 20 between the frame 12 and the C-arm 13. This guidance chain 18 helps in providing the connection line 20 with a certain stability considering that the C-arm 13 is moveable relative to the frame 12. Further, the guidance chain 18 guides the connection line 20 while the C-arm 13 is moving relative to the frame 12, such that is moves in a controlled and predictable way. The guidance chain 18 comprises a plurality of chain elements 19 (only some of which are exemplary provided with reference signs in the figures). In this embodiment, the chain elements 19 are blocks which are aligned in a row and which are not directly connected to each other. The material they are made of is preferably plastics and more preferably PTFE ("Polytetrafluorethylen"). The chain elements 19 comprise brackets 21 in the form of pins for attaching the connection line 20 to the chain elements 19 by squeezing the connection line in between them. This way, the connection line 20 positions and connects the chain elements 19 relative to each other and aligns them in a row. Alternatively to the above, reference sign 20 could also indicate a hose accommodating a plurality of connection lines. This alternative has the advantage of an additional protection against damages to the connection lines and an improved ability of holding the connection lines together.

Figures 3A, 3B:
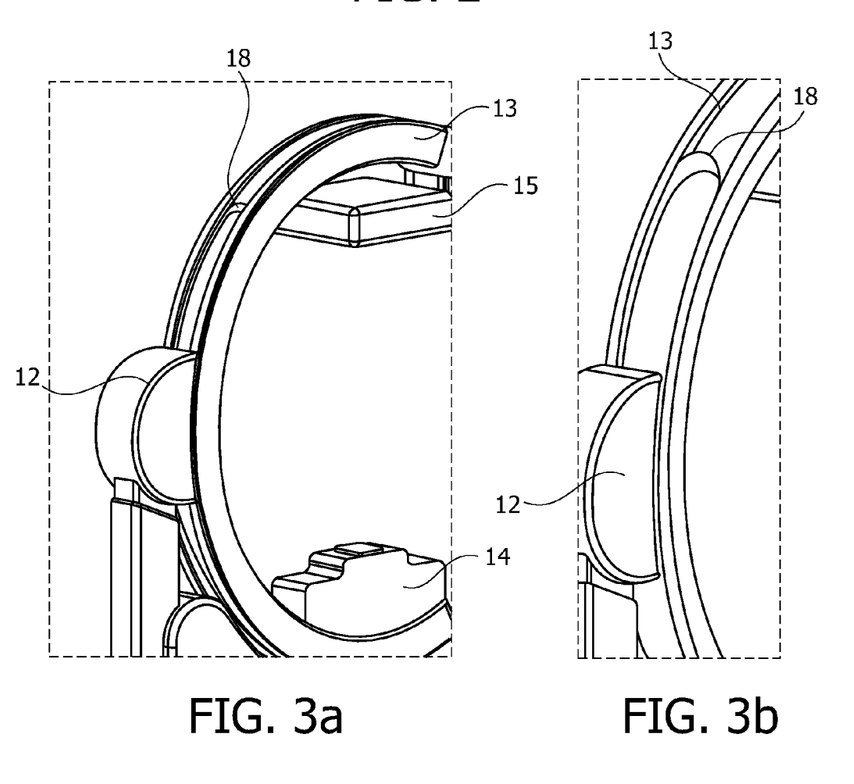
FIGS. 3a and 3b show the integration of the guidance chain into the C-arm.

FIGS. 3a and 3b show the installation of the guidance chain into the C-arm 13. The C-arm 13 has a hollow, substantially rectangular cross-section, wherein the radially outer wall (with respect to the rotation axis of the C-arm) is removed partially, such that the remaining wall at this side is large enough to support the guidance chain 18 sufficiently. Alternatively, the cross-section could also have a closed, hollow, rectangular shape. In either case, the hollow inside of the C-arm 13 forms a guiding tube for the guidance chain 18 which is thus integrated into the hollow inside of the C-arm 13. One end of the guidance chain 18 is mounted to the frame 12 (fixed chain end relative to the frame 12) and the other end of the guidance chain 18 is mounted to the C-arm 13 (moving chain end relative to the frame 12). When the C-arm 13 moves with respect to the frame 12, the guidance chain 18 is rolled on at one inner side of the C-arm profile and rolled up on the diametrically opposite inner side of it, and vice versa when reversing the direction of movement. In this specification, this movement of the guidance chain 18 is called folding movement of the guidance chain 18, wherein the guidance chain 18 forms a loop, as shown on the left side in FIG. 2. During this folding movement, the guidance chain 18 has, when looking at it in a radial direction with respect to the center of the pre-set curvature, the form of a U, wherein a U-shaped, one-sided opened loop is formed, and the remaining guidance chain end portions at both ends of the loop extent straight and in parallel to the respective other end portion.

Figure 4:
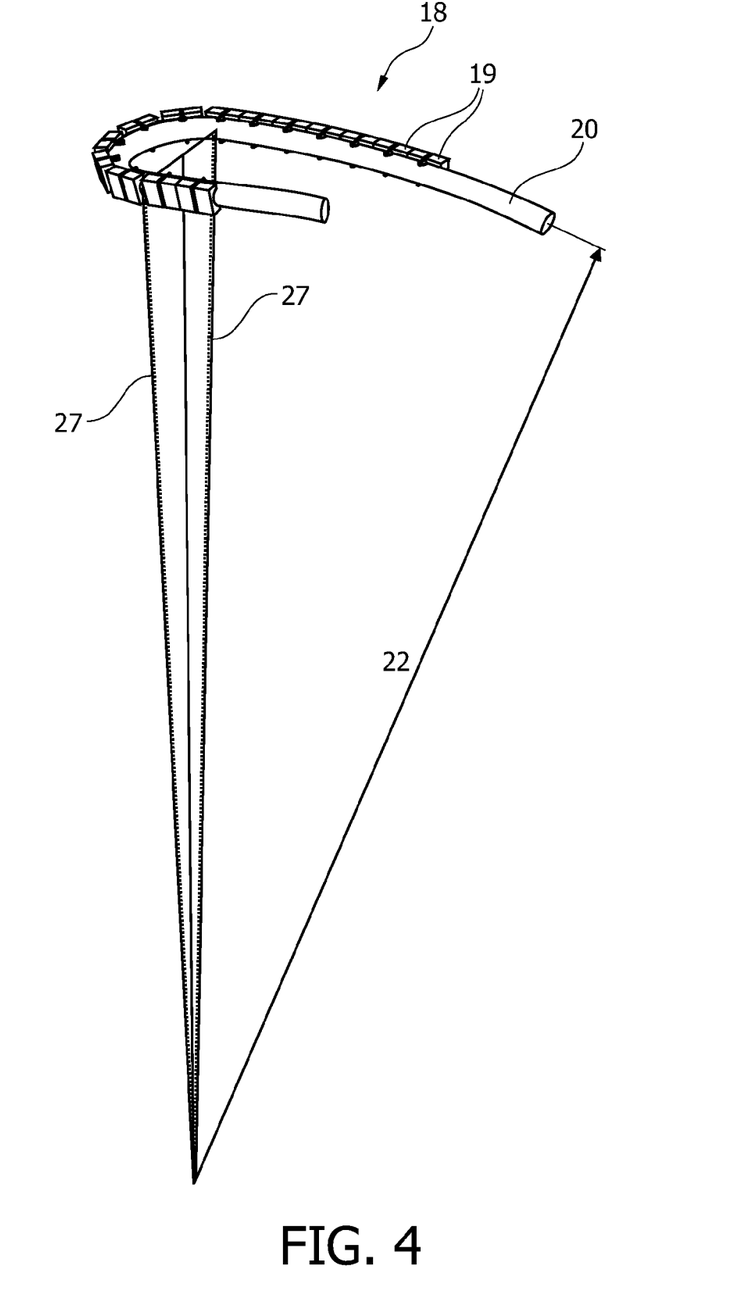
FIG. 4 shows another aspect of the guidance chain according to an embodiment of the invention.

FIG. 4 shows another aspect of the guidance chain 18 according to an embodiment of the invention. The arrow 22 indicates a radius of the guidance chain 18 along an unfolded portion, wherein the origin of the arrow 22 substantially corresponds to the center of the semi-circular shape of the C-arm 13. Preferably, the radius 22 of the guidance chain 18 corresponds to the radius of the tube formed by the hollow inside of the C-arm 13. The real or imaginary rotation axes are the axes about which consecutive chain elements 19 are rotated when describing the loop, as shown on the left side of FIGS. 2 and 4, during the folding movement. In the folded and unfolded state, the imaginary extensions of the rotation axes of the individual chain elements 19 form radial lines which are originating from the same point, and along the folded portion these radial lines form a cone shape wherein the radial lines intersect each other in the vertex of the cone shape, as indicated by the radial lines with reference sign 27 in FIG. 4. This means, the radial extensions of the rotation axes of the chain elements 19 along the folded portion and along the unfolded portion of the guidance chain 18 originate from the same point. This point is also the center of curvature of the guidance chain 18. Along the unfolded portion of the guidance chain 18, the extensions of the rotation axes are included within one plane and intersect each other in the same point.

For reasons of lucidity, some definitions are given, which apply throughout the entire specification:
the longitudinal direction of the C-arm 13 is the direction along the material of the C-arm 13 (which is a curve) from the X-ray source 14 to the X-ray detector 15, or vice versa;
the longitudinal direction of the guidance chain is the direction along the guidance chain from one end of the guidance chain to the other end of the guidance chain;
the longitudinal direction of the chain elements is the direction along the guidance chain from one end of the guidance chain to the other end of the guidance chain;
the inner longitudinal side of the chain element is the side facing inwards (towards the center of the loop) when being located right in the loop during the folding movement;
the outer longitudinal side of the chain element is the side facing in the opposite direction as the inner longitudinal side;
the radially inner side of the chain element is the side facing the rotation axis of the C-arm 13, or in other words, facing radially inwards with respect to the pre-set curvature of the guidance chain;
the radially outer side of the chain element is the side facing away from the rotation axis of the C-arm 13, or in other words, facing radially outwards with respect to the pre-set curvature of the guidance chain;
the lateral sides of the chain elements are the sides at the longitudinal ends of the chain elements.

The above mentioned curvature can be realized in the present embodiment by dimensioning the blocks forming the individual chain elements 19, such that their radially outer sides are longer in a longitudinal direction than their radially inner sides. Thus, when the connected or non-connected blocks forming the chain elements 19 contact each other at their longitudinal ends, the pre-set curvature is formed in an unfolded state of the guidance chain 18. Further, the radially inner sides of the chain elements 19 and/or the radially outer sides of the chain elements 19 can also be provided with a curvature corresponding to the curvature of the tube formed by the hollow inside of the C-arm 13 or the curvature of the surface of the C-arm 13 the respective side of the chain element 19 comes in contact with or is placed on.

Figure 5A:
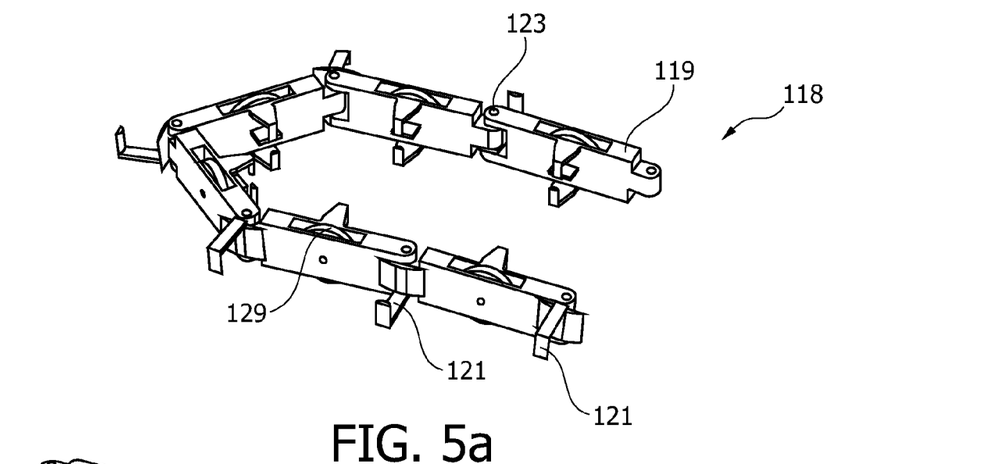
FIGS. 5a to 5c illustrate another embodiment of the guidance chain according to the invention.
Figure 5B:
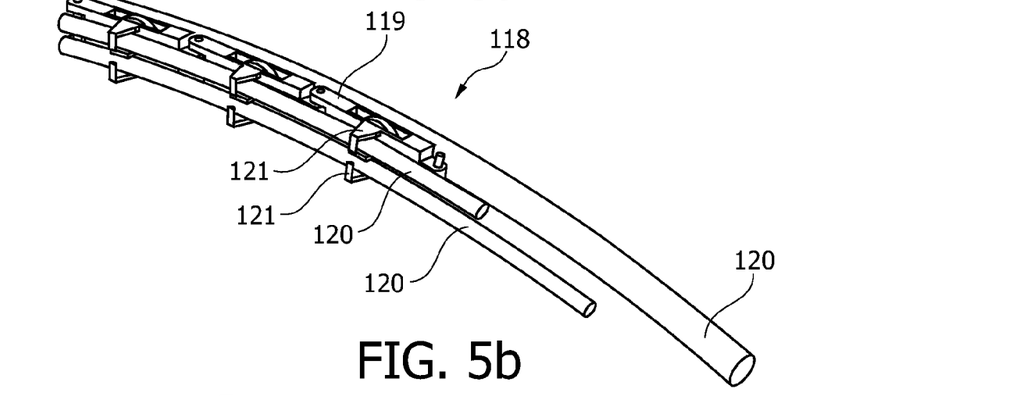
Figure 5C:
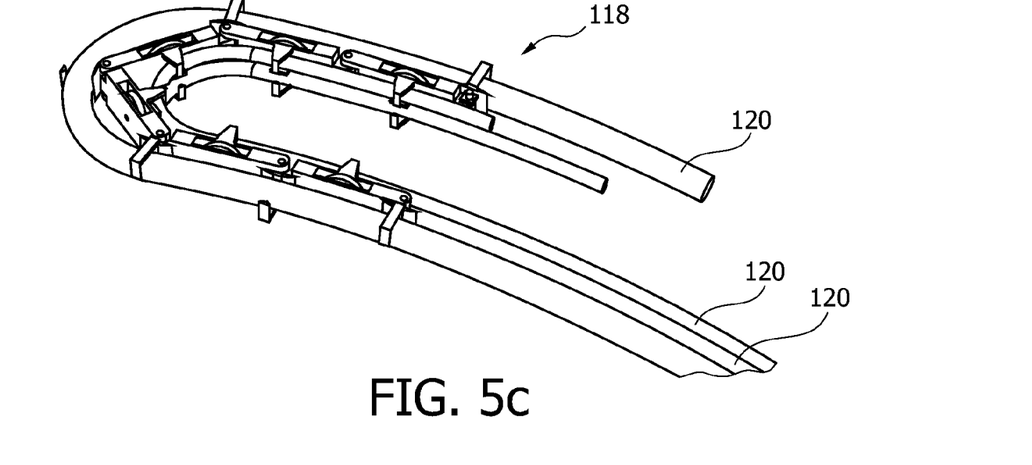

In order to avoid repetitions, in the following, only certain aspects of the embodiment are mentioned, wherein for the remaining aspects, the above described applies. FIGS. 5a to 5c illustrate another embodiment of the guidance chain according to the invention. The guidance chain 118 according to this embodiment is formed by a plurality of chain elements 119 in the form of blocks, wherein a hinge 123 connects consecutive blocks, respectively. In order to achieve the above-described curvature of the guidance chain 118, the axes of the hinges 123 form real rotation axes of the chain elements 119 and are aligned such that they intersect each other at the origin of the radius of curvature (the origin of the arrow 22 in FIG. 4). Additionally, the blocks of the chain elements 119 can be dimensioned as described above with a radially outer side being longer than a radially inner side. Further additionally, one or both longitudinal sides can be curved as described in connection with FIG. 4. These dimensioning aspects can also be provided in the following embodiments even if not explicitly mentioned in order to avoid repetitions.

The chain elements 119 are provided on the inner longitudinal side and the outer longitudinal side with brackets 121 for holding the connection lines 120. Additionally, the hinges 123 or blocks forming the chain elements 119 can be provided with abutment surfaces such that they allow only a rotation of a certain angle for limiting the bending radius of the connection lines 120 in the loop during the folding movement, in order to avoid damage to the connection lines 120 by bending them too much what could increase abrasion. Further, the chain elements 119 are provided with rolling elements 129, such as wheels, their rolling direction is parallel to the longitudinal direction of the chain elements 119. The diameter of the rolling elements 129 is larger than a width of the chain elements, such that they project from the radially inner and radially outer side of the chain elements 119.

Figure 6:
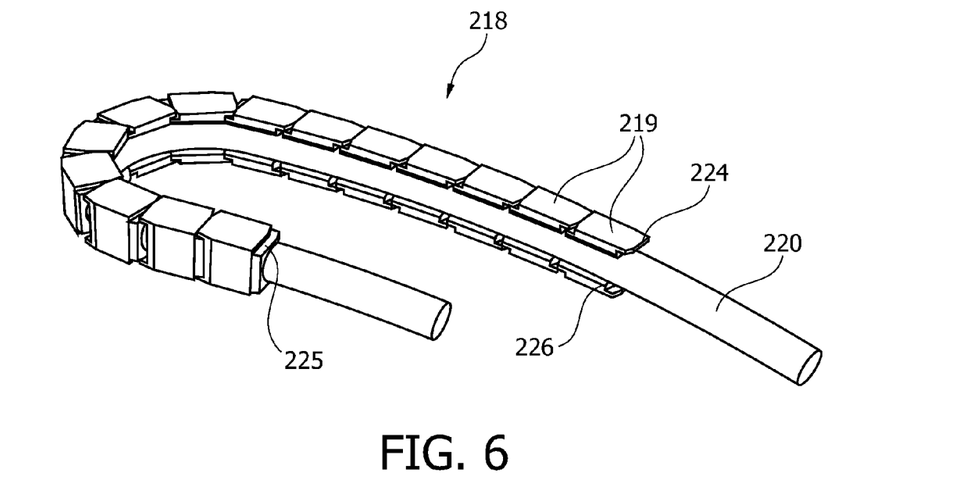
FIG. 6 shows another embodiment of the guidance chain according to the invention.

FIG. 6 shows another embodiment of the guidance chain 218 according to the invention. According to this embodiment, the chain elements 219 are provided with protrusions 224 at one longitudinal end and with corresponding recesses 225 at the other longitudinal end. These protrusions 224 of a chain element 219 fit into the recesses 225 of a consecutive chain element 219 in order to stabilize and align these chain elements 219 in a direction parallel to the imaginary rotation axes of the chain elements 219. Thus, the chain elements 219 of this embodiment are not mounted to each other, but only fitted into each other. These chain elements 219 are basically U-shaped surrounding the connection line 220, wherein the U-shape is opened on the inner longitudinal side. In order to hold the connection line 220 inside the U-shape, the ends at the opened side are provided with protrusions 226 narrowing the opening.

Figure 7:
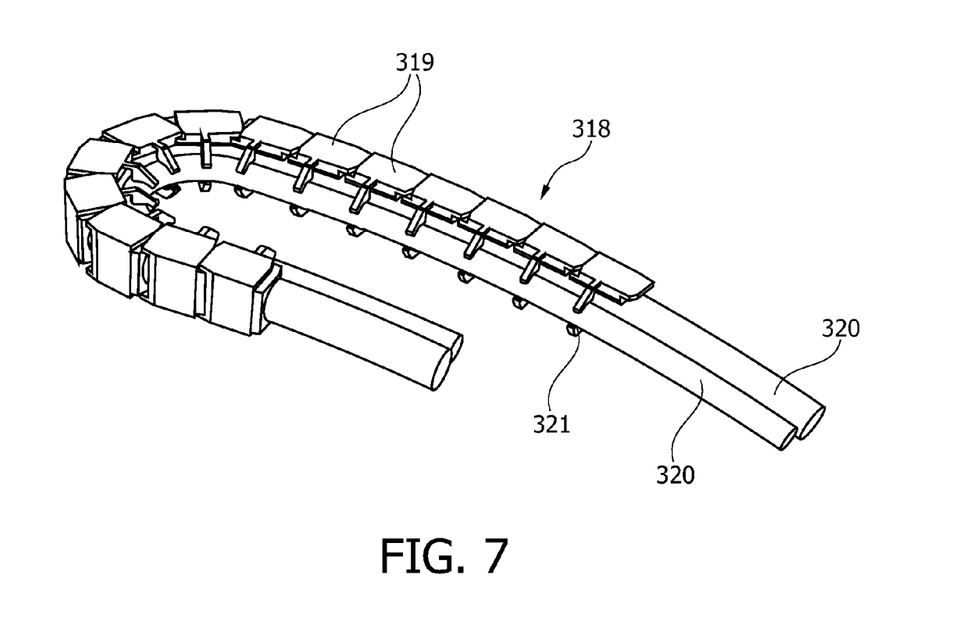
FIG. 7 illustrates a further embodiment of the guidance chain according to the invention.

FIG. 7 illustrates a further embodiment of the guidance chain 318 according to the invention. The guidance chain 318 corresponds to the one shown in FIG. 6 and described above, wherein the chain elements 319 of the guidance chain 318 additionally comprise brackets 321 which protrude from the ends of the opened side of the chain elements 319. The brackets 321 are formed like pins that are tapered at the outside towards their distal ends. On the inside, the brackets 321 are rounded in conformity to the diameter of the connection line 320 to be held by the brackets 321.

Figure 8A:
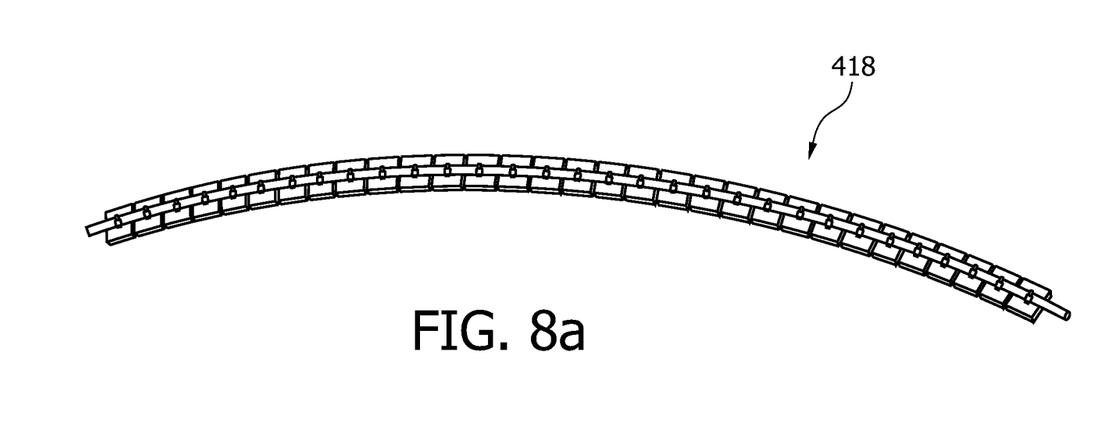
FIGS. 8a to 8d illustrate a guidance chain used for conducting experiments.
Figure 8B:
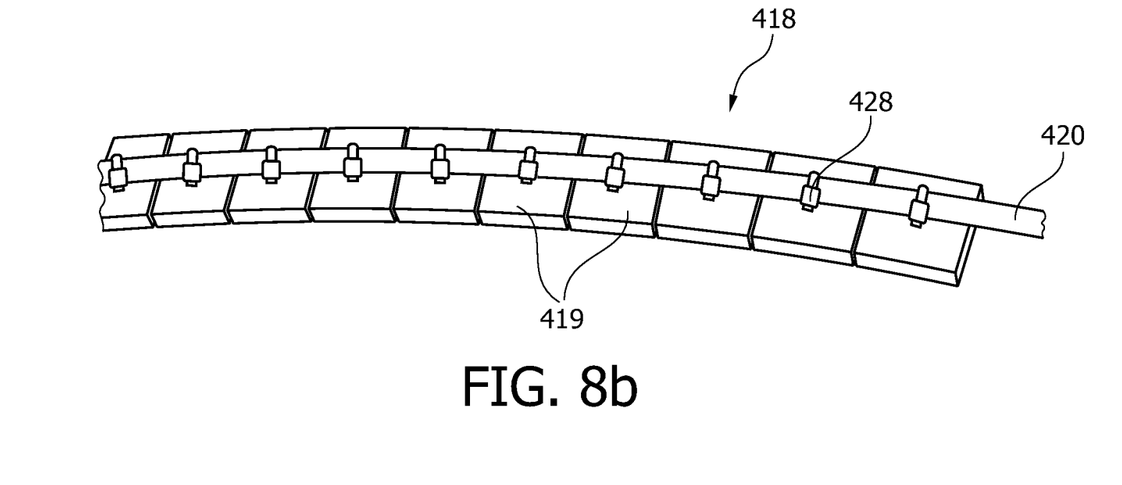
Figure 8C:
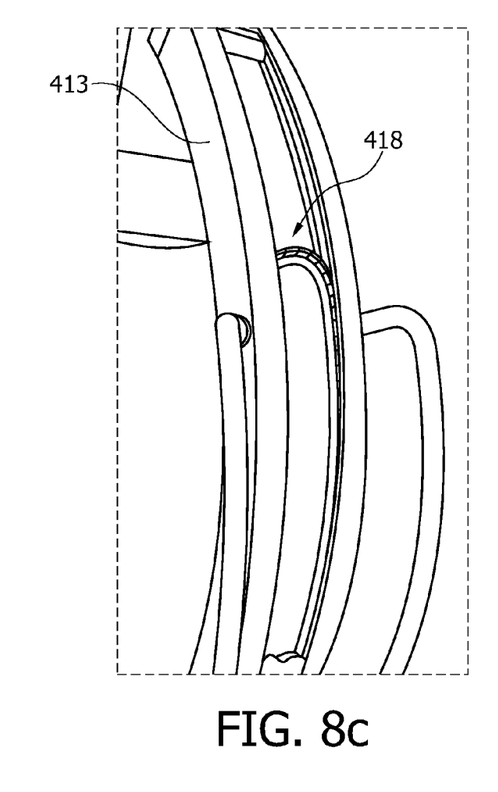
Figure 8D:
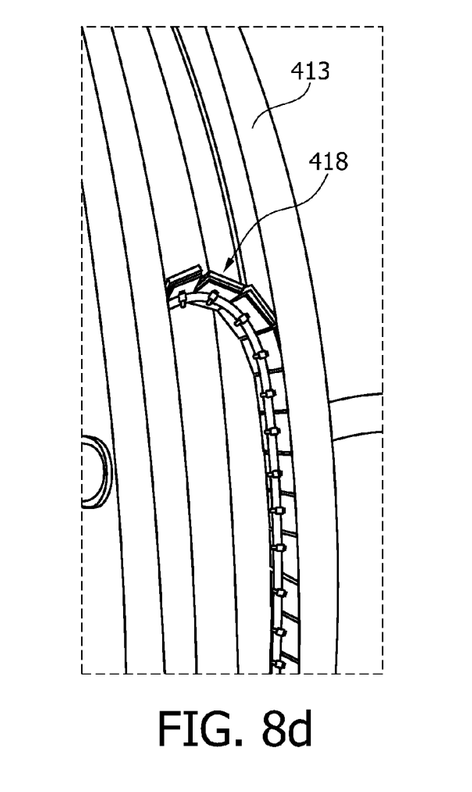

FIGS. 8a to 8d illustrate a guidance chain 418 used for conducting experiments. This guidance chain 418 is composed of chain elements 419 being blocks, the radially outer side is longer in the longitudinal direction as the radially inner side, in order to achieve the desired curvature of the guidance chain 418. The connection line 420 is attached to the inner longitudinal side of the chain elements 419 by a cable strap 428, respectively. FIGS. 8c and 8d show the installation of the guidance chain 418 into the C-arm 413 as described above.

Figure 9:
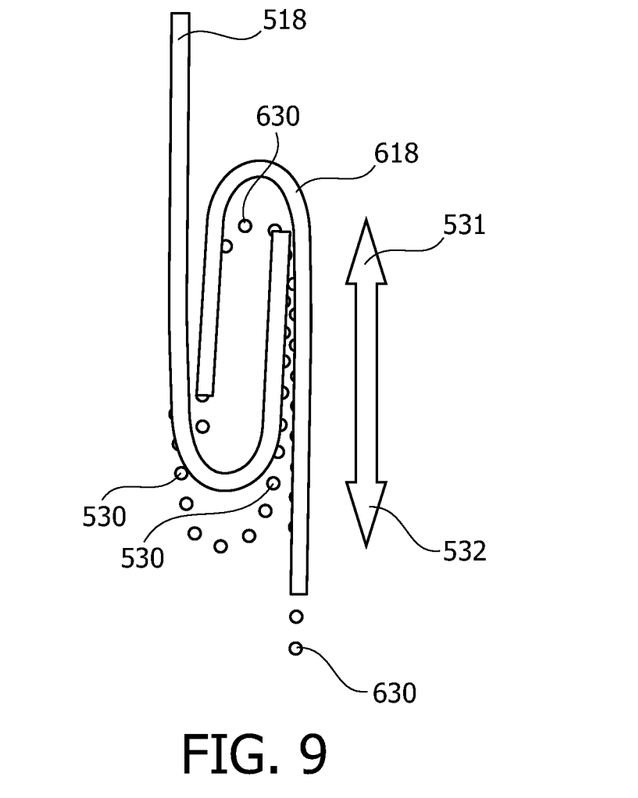
FIG. 9 schematically illustrates the integration of two guidance chains into one C-arm according to another embodiment of the invention.

FIG. 9 schematically shows another embodiment of the invention. According to this embodiment, two guidance chains 518 and 618 are arranged in the hollow inside of the single C-arm 13. The two guidance chains 518 and 618 preferably have the same pre-set curvature (with the radius indicated with 22 in FIG. 4), but are oriented in opposite directions. This opposite orientation means, that their loops face in opposite directions, i.e. the loop of the guidance chain 518 points in the direction indicated by arrow 532 and the loop of the guidance chain 618 points in the direction indicated by the arrow 531. In other words, the two guidance chains 518 and 618 are arranged such that they overlap with respect to the longitudinal direction of the C-arm 13, wherein the non-overlapping end portions of the guidance chains 518 and 618 point in opposite directions.

In this embodiment, the lower end of the guidance chain 518, as illustrated in FIG. 9, and the upper end of the guidance chain 618, as illustrated in FIG. 9, are fixed relative to the C-arm 13. The other ends of the guidance chains 518 and 618 are fixed relative to the frame 12, or to another part which the C-arm 13 is moveable relative thereto, respectively. When the C-arm 13 is moved in the direction indicated by the arrow 532, then the guidance chain 518 moves to a position, indicated by dots 530. At the same time, the guidance chain 618 is moved to a position, indicated by dots 630.

While the invention has been illustrated and described in detail in the drawings and foregoing description, such illustration and description are to be considered illustrative or exemplary and not restrictive and it is not intended to limit the invention to the disclosed embodiments. The mere fact that certain measures are recited in mutually different dependent claims does not indicate that a combination of these measures cannot be used advantageously. Any reference signs in the claims should not be construed as limiting the scope of the invention.

The invention claimed is:

1. A guidance chain for guiding at least one connection line between parts of a medical diagnostic apparatus, the parts being moveable relative to each other, the guidance chain comprising:
   a plurality of consecutive chain elements having radially inner and outer sides, wherein the consecutive chain elements are moveable relative each other about a rotation axis for producing a folding movement of the guidance chain and folded and unfolded portions of the guidance chain;
   wherein the chain elements are positioned on the folded and unfolded portions of the guidance chain at a pre-set curvature and have radial extensions of the rotation axes along the folded and unfolded portions originating from substantially the same point.

2. The guidance chain according to claim 1, wherein the pre-set curvature of the guidance chain is produced by the chain elements having a smaller longitudinal length on the radially inner sides than on the radially outer sides.

3. The guidance chain according to claim 1, further comprising hinges for connecting the consecutive chain elements.

4. The guidance chain according to claim 1, wherein the chain elements include rolling elements.

5. The guidance chain according to claim 1, wherein the plurality of consecutive chain elements include longitudinal ends having one of protrusions and recesses corresponding to one of the respective recesses or protrusions included on the longitudinal end of a following consecutive chain element such that the chain elements are aligned relative to each other.

6. The guidance chain according to claim 1, wherein chain elements are held together by the at least one connection line to which the chain elements are attached.

7. The guidance chain according to claim 1, wherein the chain elements include at least one longitudinal side having at least one bracket for holding the at least one connection line to be guided.

8. A medical diagnostic apparatus comprising:
   a frame;
   a curved member rotatable relative to the frame; and
   a guidance chain for guiding at least one connection line passing between the frame and the curved member, the guidance chain including
      a plurality of consecutive chain elements having radially inner and outer sides, the consecutive chain elements are moveable relative each other about a rotation axis for producing a folding movement of the guidance chain and folded and unfolded portions of the guidance chain, wherein the chain elements are positioned on the folded and unfolded portions of the guidance chain at a pre-set curvature and have radial extensions of the rotation axes along the folded and unfolded portions originating from substantially the same point, wherein the guidance chain is in contact with the curved member along a contacting surface, and wherein the pre-set curvature of the guidance chain is adapted to the curvature of the curved member at the contacting surface.

9. The medical diagnostic apparatus according to claim 8, wherein the guidance chain is integrated into the curved member.

10. The medical diagnostic apparatus according to claim 8, wherein the curvature of the guidance chain is produced by providing sides of the chain elements facing the contacting surface with a curvature which substantially corresponds to the curvature of the curved member.

11. The medical diagnostic apparatus according to claim 8, wherein the curved member forms a duct which supports the guidance chain in directions perpendicular to the longitudinal direction of the curved member.

12. The medical diagnostic apparatus according to claim 8, wherein the curved member forms a duct which accommodates two guidance chains arranged such that they overlap with respect to the longitudinal direction of the curved member and the non-overlapping end portions of which point in opposite directions along the longitudinal direction of the curved member.

13. The medical diagnostic apparatus according to claim 8, wherein the curved element is a C-arm of an X-ray tube.

\* \* \* \* \*